US008948473B2

(12) United States Patent
Ishikawa et al.

(10) Patent No.: US 8,948,473 B2
(45) Date of Patent: Feb. 3, 2015

(54) IMAGE PROCESSING APPARATUS AND IMAGE PROCESSING METHOD

(75) Inventors: Ryo Ishikawa, Kawasaki (JP); Yukio Sakagawa, Tokyo (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 812 days.

(21) Appl. No.: 12/534,412

(22) Filed: Aug. 3, 2009

(65) Prior Publication Data

US 2010/0074488 A1   Mar. 25, 2010

(30) Foreign Application Priority Data

Sep. 25, 2008   (JP) ................................ 2008-246591

(51) Int. Cl.
*G06K 9/00*   (2006.01)
*G06F 19/00*   (2011.01)

(52) U.S. Cl.
CPC .................................. *G06F 19/321* (2013.01)
USPC ........................................................ 382/128

(58) Field of Classification Search
None
See application file for complete search history.

(56) References Cited

U.S. PATENT DOCUMENTS

| 4,945,476 | A  | * | 7/1990 | Bodick et al. ............... 600/301 |
| 5,891,418 | A  | * | 4/1999 | Sharma .................... 424/1.69 |
| 6,108,635 | A  | * | 8/2000 | Herren et al. .................. 705/2 |
| 6,609,135 | B1 | * | 8/2003 | Omori et al. ..................... 1/1 |
| 7,110,587 | B1 | * | 9/2006 | Natanzon et al. ............ 382/131 |
| 7,418,120 | B2 | * | 8/2008 | Weiner et al. ............... 382/128 |
| 7,536,644 | B2 | * | 5/2009 | Fowkes et al. ............... 715/720 |
| 2002/0021828 | A1 | * | 2/2002 | Papier et al. ................. 382/128 |
| 2002/0111932 | A1 | * | 8/2002 | Roberge et al. .................. 707/1 |
| 2002/0175910 | A1 | * | 11/2002 | Toda ............................ 345/418 |
| 2004/0068193 | A1 | * | 4/2004 | Barnes et al. ................ 600/476 |
| 2004/0087838 | A1 | * | 5/2004 | Galloway et al. ............ 600/300 |
| 2004/0220831 | A1 | * | 11/2004 | Fabricant ........................ 705/2 |
| 2004/0254496 | A1 | * | 12/2004 | Itagaki ......................... 600/547 |
| 2005/0107689 | A1 | * | 5/2005 | Sasano ......................... 600/425 |
| 2005/0259505 | A1 | * | 11/2005 | Grand et al. ................. 365/233 |

(Continued)

FOREIGN PATENT DOCUMENTS

| JP | 2000-287013 | 10/2000 |
| JP | 2001-155099 | 6/2001 |
| JP | 2003-033327 | 2/2003 |
| JP | 2004-078299 | 3/2004 |
| JP | 2005-160502 | 6/2005 |

(Continued)

OTHER PUBLICATIONS

1. Robb et al (Patient Specific anatomic models from three dimensional medical image data for clinical applications in surgery and endoscopy); Aug. 1997.*

(Continued)

*Primary Examiner* — Nancy Bitar
(74) *Attorney, Agent, or Firm* — Fitzpatrick, Cella, Harper & Scinto (57) ABSTRACT

A plurality of sets each including part information representing a human body part and a schema image serving as the schematic view of the human body part are held. A captured image representing the interior of the body of a patient is acquired. Hierarchical structure information is acquired, which contains part information globally representing a part corresponding to a designated portion on the captured image and part information locally representing the part corresponding to the designated portion. A set including the part information contained in the hierarchical structure information is acquired. A schema image included in the acquired set is output.

11 Claims, 6 Drawing Sheets

(56) References Cited

U.S. PATENT DOCUMENTS

| | | | |
|---|---|---|---|
| 2006/0242143 A1* | 10/2006 | Esham et al. | 707/6 |
| 2006/0259505 A1* | 11/2006 | Nodate et al. | 707/102 |
| 2006/0269112 A1* | 11/2006 | Ochi | 382/128 |
| 2007/0237377 A1* | 10/2007 | Oosawa | 382/128 |
| 2008/0039707 A1* | 2/2008 | Sugiyama et al. | 600/407 |
| 2008/0058611 A1* | 3/2008 | Tsubura | 600/300 |
| 2008/0154952 A1* | 6/2008 | Waldinger et al. | 707/104.1 |
| 2009/0112627 A1* | 4/2009 | Berkman et al. | 705/3 |

FOREIGN PATENT DOCUMENTS

| | | |
|---|---|---|
| JP | 2006-318154 | 11/2006 |
| JP | 2007-089645 | 4/2007 |

OTHER PUBLICATIONS

JP2004-078299 Translation, masuda et al; Aug. 9, 2992.*
Office Action dated Jan. 25, 2013, issued in counterpart Japanese Patent Application No. 2008-246591; summary of relevance given above.

* cited by examiner

IMAGE PROCESSING APPARATUS AND IMAGE PROCESSING METHOD

BACKGROUND OF THE INVENTION

1. Field of the Invention

The present invention relates to a technique of searching for a desired schema.

2. Description of the Related Art

Before medical documents such as a medical record and diagnostic imaging report were digitized, a user drew a schema (image representing the positional relationship of a disorder portion in the structure of the human body) by hand on a medical paper document. These days, digitization of medical documents is gradually spreading along with popularization of medical information systems including a hospital information system (HIS) and picture archiving and communication system (PACS). That is, diagnosis support apparatuses are coming into use. This apparatus can create electronic medical documents such as a medical record and diagnostic imaging report, which the user wrote by hand before. Further, the apparatus can communicate with other medical information systems.

When creating an electronic medical document, a user can relatively easily input a text with a keyboard. To draw a figure with an arbitrary shape, the user manipulates an input device such as a mouse or tablet to input the trace as line information. However, the user cannot easily draw a schema with a mouse or tablet because he needs to draw a human body structure with a complicated shape.

According to a technique disclosed in patent reference 1 (Japanese Patent Laid-Open No. 2006-318154), many schema templates (to be referred to as schema images hereinafter), which are schematic views of human body parts, are stored in an apparatus. The user can select a desired one of the stored schema images. This technique allows the user to easily create a schema by selecting a schema image and drawing a simple figure on the schema image to represent a disorder portion.

Patent reference 2 (Japanese Patent Laid-Open No. 2007-89645) discloses a technique of analyzing a captured image to select a corresponding schema image. By this technique, the user can attach a desired schema image to a medical document without selecting it.

Communication protocols dedicated to captured image data have been standardized to connect image diagnosis apparatuses, medical information servers, and medical information viewers manufactured by different manufacturers. An example of the protocols is DICOM (Digital Imaging and Communications in Medicine). The DICOM standard defines in detail the contents and data structure of medical information such as image information and patient information, the procedures to communicate medical information (i.e., the procedures to request services for save, extraction, printing, and inquiry of images), the interface, and the like. DICOM is becoming an international standard in the field of medical images today. For example, patent reference 3 (Japanese Patent Laid-Open No. 2000-287013) discloses a technique associated with a DICOM-compliant image communication method and apparatus.

The technique described in patent reference 1 has an effect of facilitating selection of a desired schema image by a user because a plurality of schema images are recorded hierarchically. However, as the number of recorded schema images increases, the user needs to do a cumbersome operation to select a desired schema image from them.

The technique described in patent reference 2 can automatically select a schema image based on analysis of a display image without selecting a schema image by a user. However, a schema image the user wants to attach to a medical document is not always uniquely determined from a captured image displayed by him. In particular, selection of a schema image does not reflect a portion to which the user pays attention on a captured image.

SUMMARY OF THE INVENTION

The present invention has been made to solve the above-described problems, and provide a mechanism of selecting a desired schema image based on input of a designated portion on a captured image by a user.

According to the first aspect of the present invention, an image processing apparatus comprising:

a holding unit which holds a plurality of sets each including part information representing a human body part and a schema image serving as a schematic view of the human body part;

a unit which acquires a captured image representing an interior of a body of a patient;

a unit which acquires hierarchical structure information containing part information globally representing a part corresponding to a designated portion on the captured image and part information locally representing the part corresponding to the designated portion;

an acquisition unit which acquires, from the holding unit, a set including the part information contained in the hierarchical structure information; and an output unit which outputs a schema image included in the set acquired by the acquisition unit.

According to the second aspect of the present invention, an image processing method of an image processing apparatus for holding a plurality of sets each including part information representing a human body part and a schema image serving as a schematic view of the human body part, comprising the steps of:

acquiring a captured image representing an interior of a body of a patient;

acquiring hierarchical structure information containing part information globally representing a part corresponding to a designated portion on the captured image and part information locally representing the part corresponding to the designated portion;

acquiring a set including the part information contained in the hierarchical structure information; and outputting a schema image included in the set acquired in the acquiring step.

Further features of the present invention will become apparent from the following description of exemplary embodiments with reference to the attached drawings.

DESCRIPTION OF THE EMBODIMENTS

Embodiments of the present invention will be described in detail below with reference to the accompanying drawings. These embodiments are merely examples of the configuration of the present invention set forth in the following claims, and the present invention should not be limited to these embodiments.

First Embodiment

Figure 1:
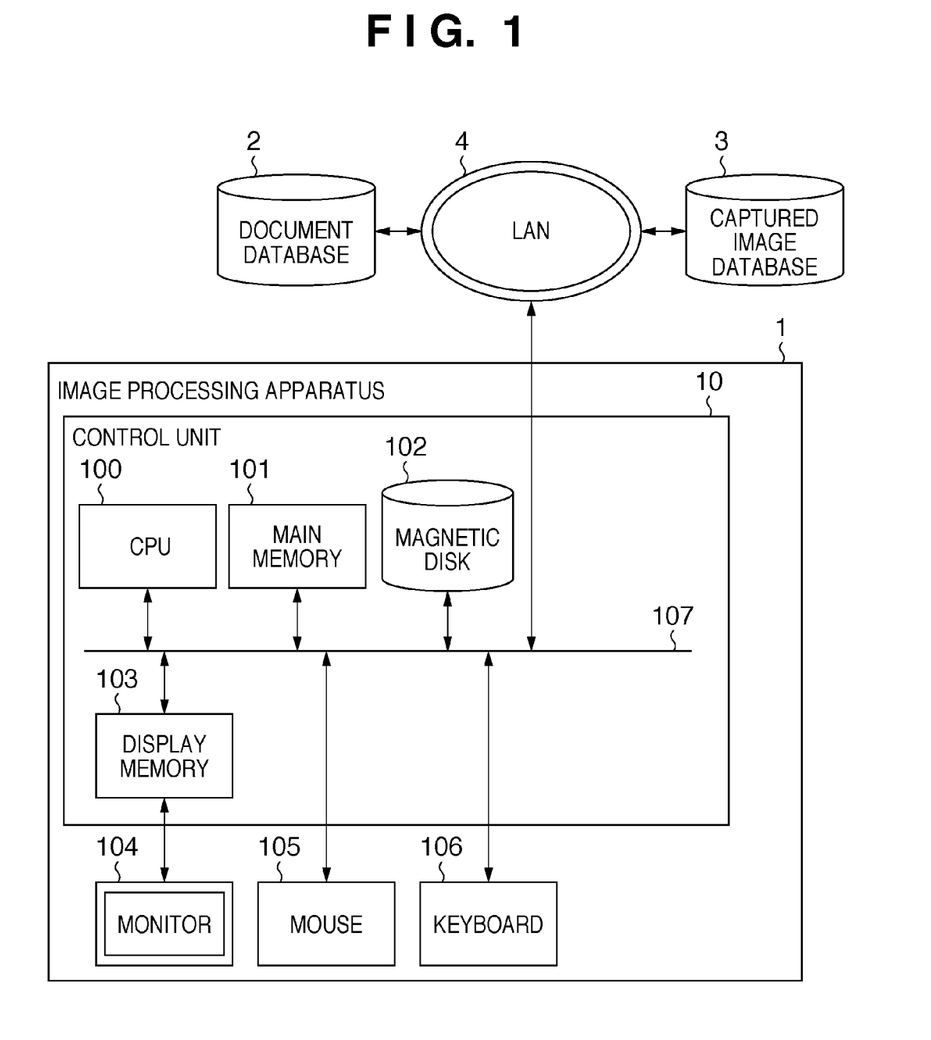
FIG. 1 is a block diagram showing the arrangement of an image processing apparatus 1.

FIG. 1 is a block diagram exemplifying the arrangement of an image processing apparatus according to the first embodiment. Referring to FIG. 1, an image processing apparatus 1 includes a control unit 10, monitor 104, mouse 105, and keyboard 106. The control unit 10 includes a CPU (Central Processing Unit) 100, main memory 101, magnetic disk 102, display memory 103, and shared bus 107. The CPU 100 executes programs stored in the main memory 101 to perform various control operations such as communication with a document database 2 and captured image database 3 and the overall control of the image processing apparatus 1.

The CPU 100 mainly controls the operation of each building component of the image processing apparatus 1 and executes each processing of the image processing apparatus. The main memory 101 stores control programs to be executed by the CPU 100 and provides a work area used when the CPU 100 executes a program. The magnetic disk 102 stores an operating system (OS), device drivers for peripheral devices, a variety of application software programs including a program to perform image processing (to be described later), schema information (to be described later), and the like. The display memory 103 temporarily stores display data for the monitor 104. The monitor 104 is, for example, a CRT monitor or liquid crystal monitor, and displays an image based on data held in the display memory 103. The mouse 105 and keyboard 106 accept a pointing input, text input, and the like from a user. These building components are communicably connected to each other via the shared bus 107.

In the first embodiment, the image processing apparatus 1 can read out documents such as an electronic medical record and diagnostic imaging report from the document database 2 via a LAN 4 under the control of the CPU 100. The image processing apparatus 1 can read out various kinds of captured image data from the captured image database 3 via the LAN 4 under the control of the CPU 100. The image processing apparatus 1 may be connected to an external storage such as an FDD, HDD, CD drive, DVD drive, MO drive, or ZIP drive to read out one or both of a document and captured image data from it. Examples of captured images are a scout roentgenogram, X-ray CT (Computed Tomography) image, MRI (Magnetic Resonance Imaging) image, PET (Positron Emission Tomography) image, SPECT (Single Photon Emission Computed Tomography) image, and ultrasonic image.

A method of controlling the image processing apparatus 1 by the control unit 10 will be explained with reference to the flowchart of FIG. 2. The CPU 100 executes a program stored in the main memory 101 to implement the following processing shown in the flowchart. The magnetic disk 102 stores an OS (Operating System) and a variety of data. The magnetic disk 102 also stores programs and data for causing the CPU 100 to control various functions of the image processing apparatus 1 or execute processes of the image processing apparatus 1. If necessary, programs and data saved in the magnetic disk 102 are loaded into the main memory 101 under the control of the CPU 100 and processed by the CPU 100. Some pieces of information stored in the main memory 101 in the above description may be saved in the magnetic disk 102. In the following processing, the user inputs various kinds of commands (designations and instructions) to the image processing apparatus 1 by manipulating the mouse 105 and keyboard 106. The monitor 104 displays the execution status and execution result of a program executed by the CPU 100.

In step S201, the CPU 100 receives a command input from the user via the mouse 105 or keyboard 106. Based on the command input, the CPU 100 selects one of existing documents and reads it into the main memory 101, or creates a new document in the main memory 101. In the document selection, the CPU 100 communicates with the document database 2 via the shared bus 107 and LAN 4 and receives a desired document from the document database 2. Alternatively, the CPU 100 can read a desired document from an external storage connected to the image processing apparatus 1.

Processing to write constituent data of a schema image at a predetermined position in the document read into the main memory 101 in step S201 will be explained.

In step S202, the CPU 100 receives a command input from the user via the mouse 105 or keyboard 106. According to the command input, the CPU 100 acquires a captured image representing the interior of the body of a patient and additional information, and stores them in the main memory 101.

In reading a captured image and additional information, the CPU 100 communicates with the captured image database 3 via the shared bus 107 and LAN 4. The CPU 100 then receives a desired captured image and its additional information from the captured image database 3. Instead, the CPU 100 can read a desired captured image and its additional information from an external storage connected to the image processing apparatus 1. The additional information includes, for example, imaging device information, captured image information such as imaging conditions, and object information such as age and sex. Additional information is generated by an imaging apparatus (not shown) and saved in association with a captured image simultaneously when the image is captured.

In the embodiment, a captured image and its additional information acquired in step S202 are recorded by the DICOM standard, but the recording format is not limited to it.

The CPU 100 can acquire a captured image and its additional information in response to a command input from the user. The CPU 100 may read a captured image associated with a document and additional information of the captured image in synchronization with acquisition of the document by the CPU 100 in step S201.

In step S203, the CPU 100 acquires the coordinates (position of interest) of a designated portion on the captured image. For example, the user designates a target portion, and the CPU 100 acquires the designated portion. First, the CPU 100 displays a captured image acquired in step S202 using, for example, the monitor 104. Then, the user uses the mouse 105 or keyboard 106 to designate a portion where a feature suspected of a disorder appears in the displayed captured image. The CPU 100 acquires the coordinates of the portion designated by the user on the captured image. The CPU 100 can also perform image processing for a captured image to automatically detect a designated portion such as a disorder portion, and acquire the coordinates of the detected designated portion on the captured image. The coordinates of a designated portion are acquired by, for example, obtaining those of a point on an image. The embodiment adopts this method. Another method acquires information which defines a region on a captured image, such as a set of image coordinates or rectangle information. Also in this case, subsequent processing can be done by handling a designated region as a plurality of points, similarly to the method of acquiring the coordinates of a point on an image.

To acquire coordinates on a captured image, the CPU 100 needs to transform acquired coordinates. For example, coordinate information input from the mouse 105 is one in a frame held in the display memory 103, and is not one on a captured image. This will be explained by exemplifying a normal coordinate system whose origin is the upper left corner of the display screen of the monitor 104. To acquire coordinates on a captured image, the x- and y-coordinate values of the upper left corner of a captured image in the entire screen need to be subtracted from acquired coordinate values. The coordinates of the upper left corner of a captured image in the entire screen may be fixed or freely changed by a user. These coordinates suffice to be obtained from the main memory 101. In some cases, a captured image is partially enlarged and displayed to observe the captured image in more detail and input a designated portion. In this case, the coordinates of a portion designated by the user on the screen need to be transformed into corresponding ones on the original image. The CPU 100 can perform the coordinate transform processing using the enlargement center of an enlarged image and enlargement magnification information. More specifically, the CPU 100 calculates a vector from the enlargement center of an enlarged image to designated coordinates. The CPU 100 divides the obtained vector value by the enlargement magnification, obtaining a vector from the enlargement center on the original image to the designated coordinates. The CPU 100 adds the vector value to the coordinate values of the enlargement center on the original image. As a result, coordinates designated by the user on the original image can be obtained.

When a captured image (3D image) containing 3D information, such as an X-ray CT image, is used, the CPU 100 can display a slice image of the 3D image on a given plane. In this case, the user designates a target portion on the slice image displayed by the CPU 100. Based on the type of slice image and the slice position on the 3D image, the CPU 100 can obtain the 3D coordinates of the portion designated by the user on the original 3D image. This processing is actually done in step S205 later. The CPU 100 saves display information 51 in the main memory 101 in order to use it in step S205. The display information 51 represents the display conditions of a slice image, for example, a plane on which an image is sliced.

The number of designated portions is not limited to one for one captured image. The user can input designated portions as a combination of points, and the CPU 100 can acquire them. For example, the user may designate a portion considered to be the primary lesion of a given disease and a portion where metastasis is suspected. In this case, the CPU 100 sequentially stores the designated portions. Upon receiving a command that the user has ended input of designated portions, the CPU 100 ends the storage processing. If the user observing a captured image cannot find out a designated portion in it, he may input a designated portion input end command without inputting a designated portion.

In step S204, the CPU 100 determines whether to switch processing in accordance with whether the user has input a designated portion in step S203. If the CPU 100 determines that the user has input a designated portion, the process advances to step S205. If the CPU 100 determines that the user has not input a designated portion, that is, there is no designated portion, the process ends.

In step S205, the CPU 100 specifies a part indicated by the designated portion on the captured image based on the captured image and its additional information acquired in step S202 and the designated portion acquired in step S203. The part may be specified as an organ name such as "stomach", "lung", "liver", or "heart", or an accurate position in an organ such as "right lung" or "left ventricle". The part can be specified not only as an organ but also as a rough part such as the chest or abdomen. For example, when the designated portion acquired in step S203 indicates the right lung, the right lung is part of the lung and part of the chest, too. That is, a designated portion corresponds not only to one part but also to a plurality of parts as described above. A processing method of specifying a part will be explained in detail with reference to FIGS. 3 to 5.

Figure 3:
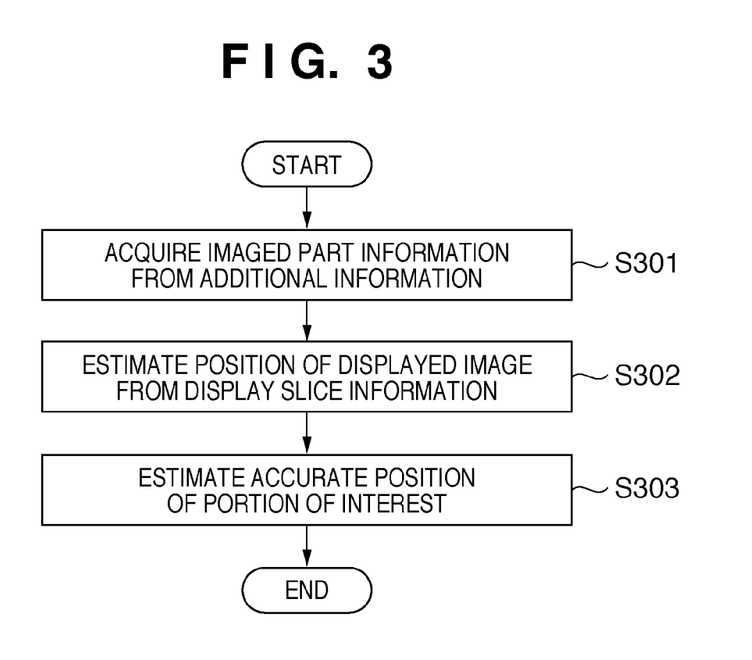
FIG. 3 is a flowchart showing processing to determine a part of the human body at a designated portion.

FIG. 3 is a flowchart for explaining the processing procedure to specify a part indicated by a designated portion acquired in step S203.

Figure 2:
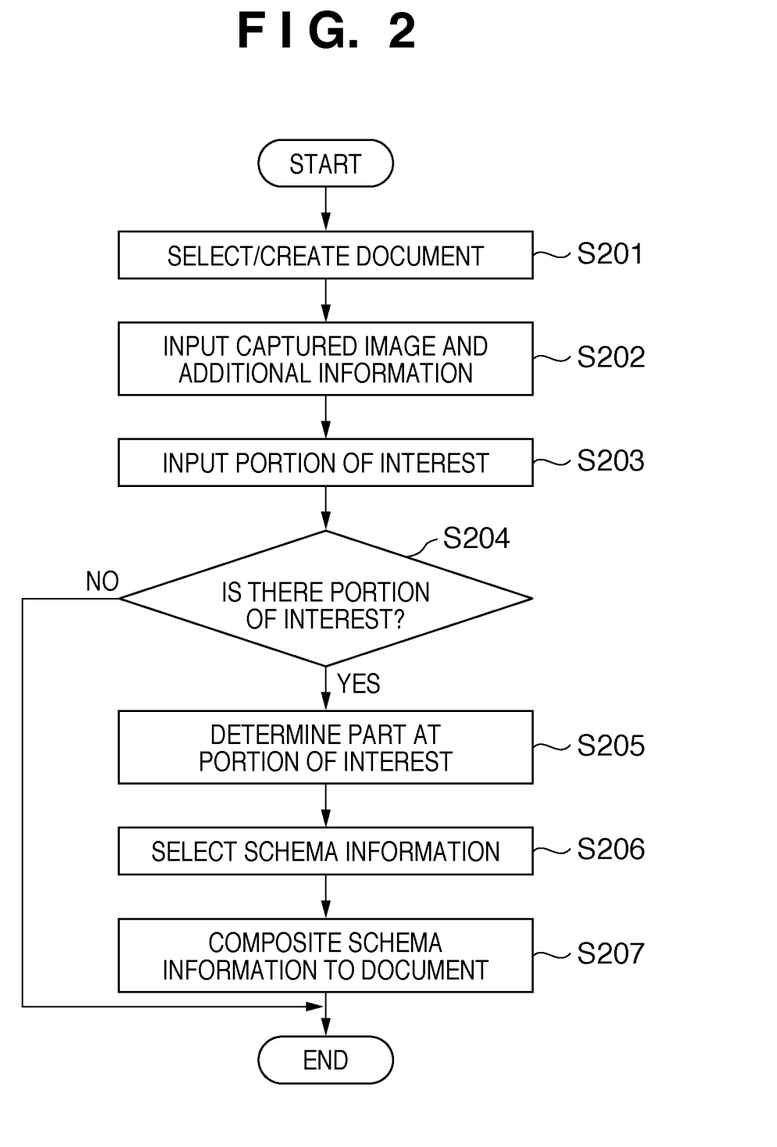
FIG. 2 is a flowchart showing the processing procedure of the image processing apparatus 1.
Figure 4:
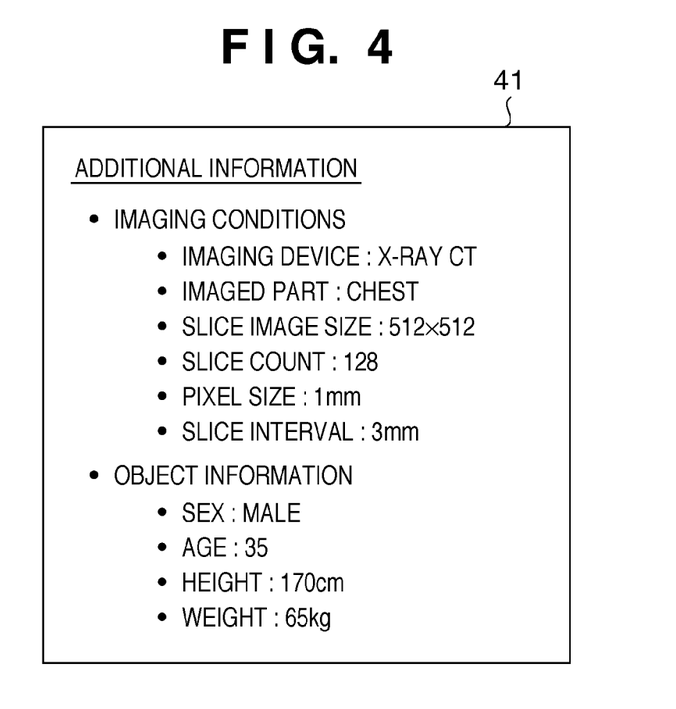
FIG. 4 is a view for explaining the imaging range of a captured image.

The CPU 100 estimates the imaging target of the captured image acquired in step S202 of FIG. 2, and the position of the imaging target. For the estimation, in step S301, the CPU 100 obtains the imaging conditions of the captured image and object information from the additional information acquired in step S202 of FIG. 2. FIG. 4 shows an example of this information. In FIG. 4, additional information 41 is an example of the additional information read in step S202. The CPU 100 can obtain imaging condition information from the additional information 41, including the items of the imaging device, imaged part, slice image size, pixel size, slice count, and slice interval. The CPU 100 can also obtain object information such as sex, age, height, and weight.

Figure 5:
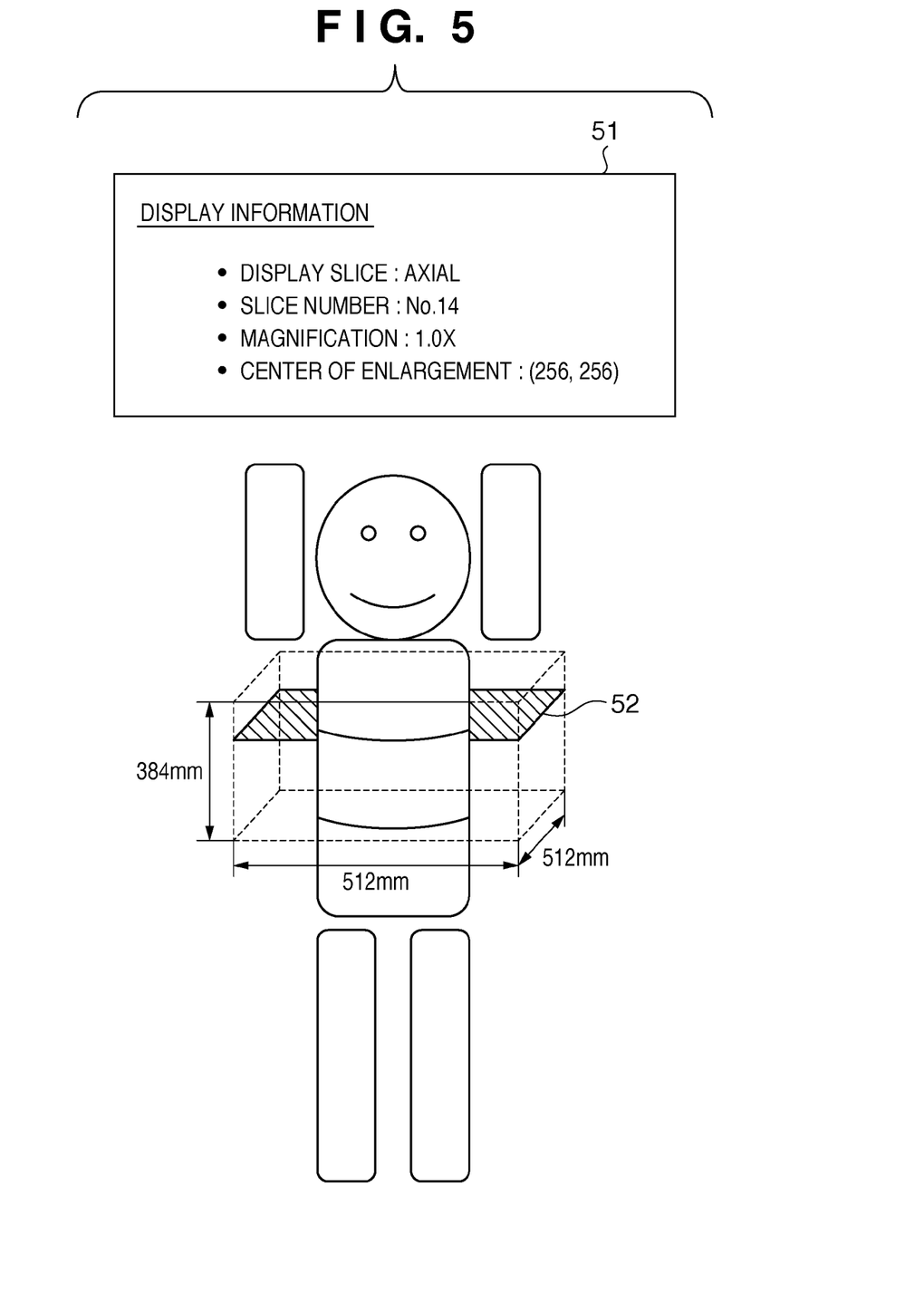
FIG. 5 is a view for explaining the display range of a captured image.

In step S302, if the captured image acquired in step S202 is a 3D image, the CPU 100 determines the position of an image in the 3D captured image that has been displayed on the screen when the user input a designated portion in step S203. In this step, the CPU 100 estimates the position of the displayed image in the 3D image from the display conditions of the image displayed when a designated portion was input in step S203. FIG. 5 is a view for explaining this processing. The display information 51 is information on the display conditions of an image displayed when a designated portion was input in step S203. The display information 51 contains the item of the type (axial, coronal, or sagittal) of display slice as display slice information. This information clarifies a direction in which the displayed captured image is sliced. In this example, the displayed captured image is a slice in a direction perpendicular (axial) to the body axis of an object. A numerical value recorded in the slice number item exhibits the number of a slice image. In this example, the 14th slice is displayed. As is apparent from the imaging condition information in FIG. 4, the slice interval is 3 mm in the embodiment. From this, the displayed slice is a section at a position of 3×14=42 mm from the top of the imaging range.

In step S303, the CPU 100 estimates a part indicated by the designated portion on the captured image based on the imaging condition information obtained in step S301 and the position information obtained in S302. The CPU 100 acquires the estimated part as hierarchical structure information.

According to an example of the estimation method, data containing a set of coordinates on a captured image and information on a human body part represented by the pixel at the coordinates is utilized for the captured image of a given patient. The data will be called standard image information. A captured image contained in the standard image information will be called a standard image. Information on a human body part represented by each pixel in the standard image will be called standard part information. A piece of standard image information holds as many sets of coordinates and standard part information as pixels (holds a plurality of sets). The standard part information contains part information representing one or a plurality of human body parts. For example, the standard part information is formed from pieces of part information representing a plurality of parts such as "left lung", "lung", "chest", and "upper half of the body", the ranges of which are different and hierarchical. The standard image information further contains the imaging conditions and object information of a standard image included in the standard image information. These pieces of information will be called standard additional information. The standard image information is held in a storage medium such as the magnetic disk 102.

Assume that the captured image acquired in step S202 is a chest roentgenogram and the user designates a pixel at coordinates (250,300) as a designated portion. In this case, the CPU 100 selects standard image information having the same imaging conditions as those of the image, that is, standard image information having standard additional information representing a chest roentgenogram. The CPU 100 acquires standard part information corresponding to the coordinates of the designated portion as hierarchical structure information from the selected standard image information. In other words, the CPU 100 acquires, as hierarchical structure information, standard part information of the coordinates (250,300) contained in the standard image information. If the standard part information of the coordinates (250,300) indicates (left lung, lung, chest, upper half of the body), the CPU 100 determines that a part at the portion designated by the user is (left lung, lung, chest, upper half of the body). The CPU 100 then acquires information (left lung, lung, chest, upper half of the body) as hierarchical structure information.

Needless to say, since the body size depends on the person, it is necessary that the storage medium stores pieces of standard image information in correspondence with the ages, sexes, and the like of objects. For example, the storage medium desirably stores pieces of standard image information of chest roentgenograms for a 10-year-old male, 10-year-old female, 30-year-old male, 30-year-old female, and the like. In this case, the CPU 100 specifies standard image information having standard additional information corresponding to additional information of the captured image acquired in step S202. For example, when additional information of the captured image acquired in step S202 contains object information (chest roentgenogram, male, age 30), the CPU 100 specifies standard image information containing the information (chest roentgenogram, male, age 30) as standard additional information. There may be no standard image information having standard additional information completely matching additional information of the captured image acquired in step S202. In this case, the CPU 100 specifies standard image information containing standard additional information partially matching additional information of the captured image acquired in step S202.

The resolution (pixels/mm) may differ between the captured image acquired in step S202 and a standard captured image. The resolution information exists in additional information of a captured image and that of standard image information. In this case, the CPU 100 divides the coordinate values of a designated portion by the resolution of the captured image, and multiplies them by the resolution of a standard captured image. As hierarchical structure information, the CPU 100 acquires standard part information associated with the calculated coordinates.

When the captured image acquired in step S202 is a 3D image, the CPU 100 acquires 3D coordinates in the 3D image based on the display slice position information acquired in step S302. The CPU 100 specifies standard image information having additional information corresponding to imaging target information represented by additional information of the captured image. The CPU 100 acquires, as hierarchical structure information, standard part information associated with coordinates corresponding to the 3D coordinates of the captured image.

A part represented by a pixel at a designated portion is estimated using standard image information. Instead, an image recognition technique can be used to estimate a specific part at a designated portion input by a user with reference to imaged part information obtained in step S302.

By executing the processes from steps S301 to S303, a specific part of the human body at the designated portion in step S205 of FIG. 2 can be determined.

In step S206, the CPU 100 selects schema information to be suitably composited to a document from pieces of schema information recorded on the magnetic disk 102 in accordance with the hierarchical structure information acquired in step S205. The schema information contains a schema image, and schema part information indicating a part represented by the schema image. A piece of schema information may contain pieces of schema part information. The schema information may similarly contain information such as the range of a schema image and the level of detail of a structure expressed by the schema image. Pieces of schema information can be recorded and managed hierarchically as disclosed in patent reference 1. In the embodiment, schema information suffices to contain at least a schema image and schema part information. In the embodiment, the magnetic disk 102 records pieces of schema information, but another recording medium such as the captured image database 3 may store them.

Figure 6:
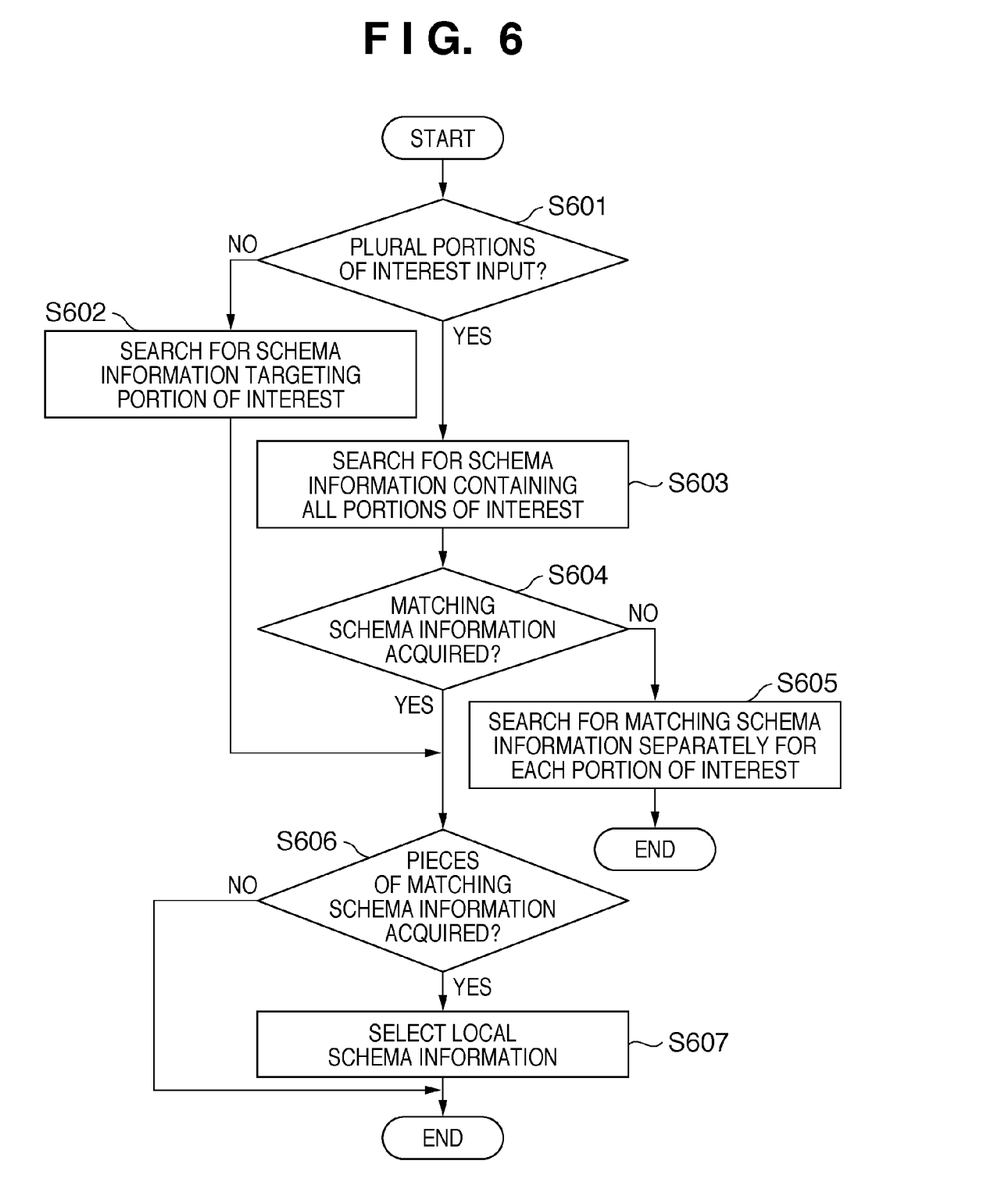
FIG. 6 is a flowchart showing processing to select schema information.

An example of the concrete processing procedure in step S206 will be described in detail with reference to FIG. 6. FIG. 6 is a flowchart for explaining the processing in step S206 of FIG. 2 in more detail.

In step S601, the CPU 100 determines whether a plurality of designated portions have been input in step S203 of FIG. 2. If a plurality of designated portions have been input, the process advances to step S603; if one designated portion has been input, to step S602.

In step S602, the CPU 100 searches the magnetic disk 102 to acquire schema information containing schema part information representing the same part as one of parts contained in the hierarchical structure information acquired in step S205. Assume that the CPU 100 has obtained in step S205 hierarchical structure information formed from pieces of part information, like (upper half of the body, chest, lung, right lung). In this case, the CPU 100 can acquire schema information containing, as schema part information, part information "chest" included in the hierarchical structure information. Pieces of schema information may have the same schema part information. In this case, the CPU 100 may acquire pieces of schema information. The main memory 101 stores the search result obtained in this processing. Thereafter, the process advances to step S606.

Step S603 is schema image search processing executed when a plurality of designated portions have been input in step S203 of FIG. 2. The CPU 100 acquires hierarchical structure information of each designated portion in step S205. The CPU 100 repeats this processing for the respective designated portions. The CPU 100 extracts part information common to the pieces of hierarchical structure information. The CPU 100 performs the same acquisition processing as in step S602 using the extracted part information, thereby obtaining a schema image representing the plurality of designated portions. After this processing, the process advances to step S604. In step S603, similar to step S602, the CPU 100 may acquire pieces of schema information. If there is no common schema information, the process advances to step S604 without acquiring schema information.

In step S604, the CPU 100 switches processing depending on whether schema information has been acquired in step S603. If at least a piece of schema information has been acquired, the process advances to step S606; if no schema information has been acquired, the process advances to step S605.

In step S606, the CPU 100 determines whether pieces of schema information have been acquired in step S602 or S603, and switches processing in accordance with the determination result. If pieces of schema information have been acquired, the process advances to step S607. If only one piece of schema information has been acquired, the processing in step S206 ends, and the process advances to step S207.

Figure 7:
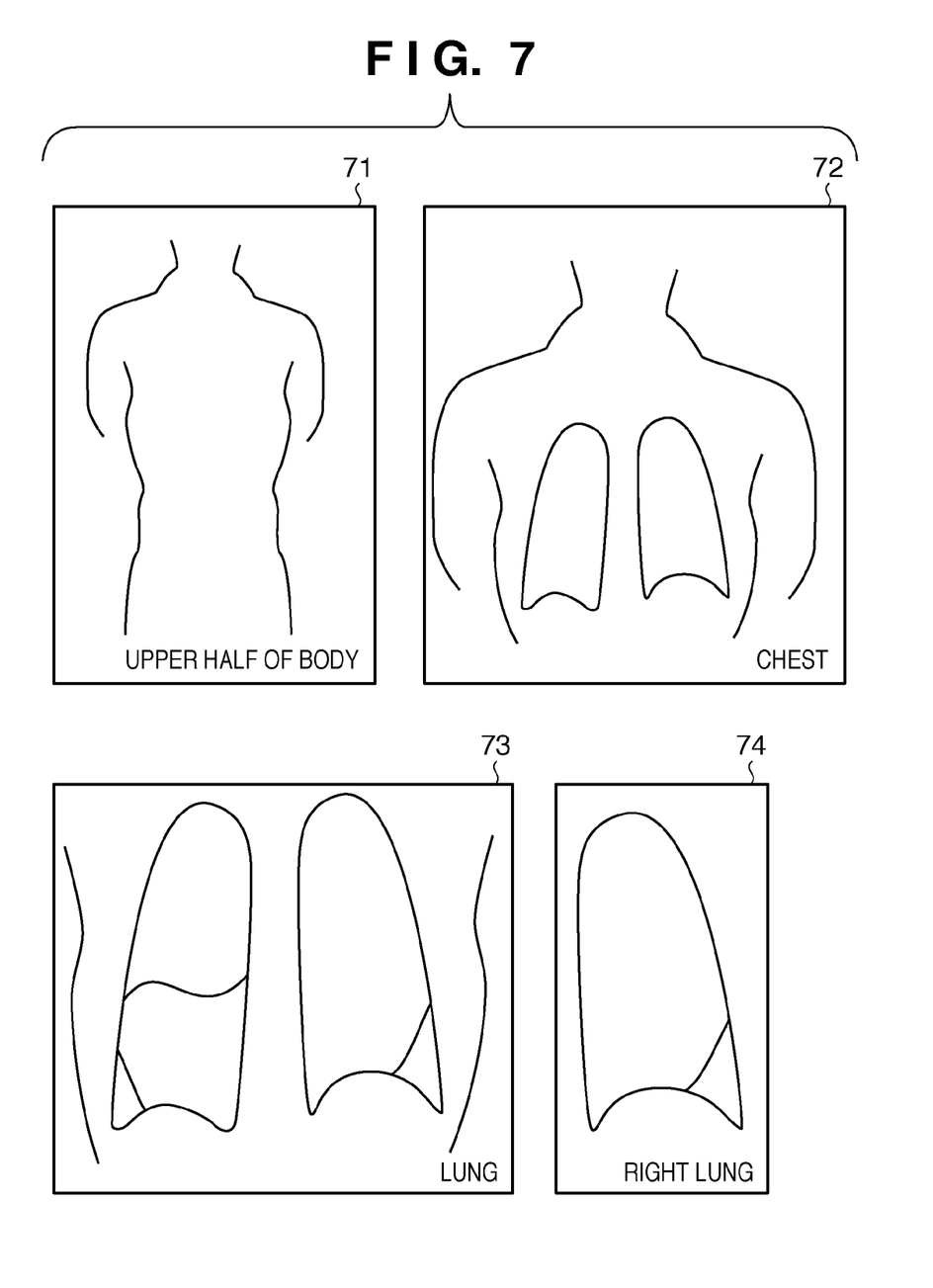
FIG. 7 is a view showing an example in which pieces of schema information exist for one portion of interest.

Step S607 is executed when pieces of schema information have been acquired in step S602 or S603. The CPU 100 selects and acquires desired one of the pieces of schema information acquired in step S602 or S603. Hierarchical structure information (upper half of the body, chest, lung, right lung) is assumed to have been acquired by the processing of step S205 for the designated portion acquired in step S203 of FIG. 2. As shown in FIG. 7, schema information 71 on the upper half of the body, schema information 72 on the chest, schema information 73 on the lung, and schema information 74 on the right lung have been acquired in step S602 or S603.

Appropriate schema information can be selected from these pieces of schema information by various methods. For example, schema information containing a schema image locally representing a designated portion is selected from pieces of schema information. This selection is made by referring to schema part information contained in schema information. For this purpose, it is necessary that a storage such as the magnetic disk 102 holds information which hierarchically arranges parts of the human body. More specifically, the storage such as the magnetic disk 102 holds hierarchical information that the upper half of the body contains the chest, the chest contains the lung, and the lung contains right and left lungs. From the hierarchical information, the CPU 100 determines that "right lung" is a more local part than "upper half of the body", "chest", and "lung". Among the pieces of schema information shown in FIG. 7, the CPU 100 determines the schema information 74 on the right lung as schema information containing a schema image locally representing the designated portion. The CPU 100 selects the schema information 74 on the right lung.

As another method, the CPU 100 may select schema information having a schema image of a higher level of detail than those of pieces of schema information acquired in step S602 or S603. To achieve this method, schema information suffices to include information indicating the level of detail of a schema image. The level of detail can be set in advance for each schema image so that it becomes higher for a global schema image than for a local one. After schema information is selected and acquired by the above-described processing, the process advances to step S207 in FIG. 2.

Step S605 is executed when the CPU 100 could not acquire a schema image representing all designated portions in the processing of step S603. In this step, the CPU 100 searches for schema information corresponding to each of the acquired designated portions. That is, the CPU 100 performs steps S602 and S606, and if necessary, step S607 for each designated portion. As a result of the processing in step S605, the CPU 100 acquires pieces of schema information.

As another processing in step S605, designated portions may be partially combined instead of separately searching for schema information which matches each designated portion. For example, when there are three designated portions A, B, and C, schema information common to A and B and that corresponding to C are acquired in place of acquiring pieces of schema information corresponding to the respective designated portions A, B, and C. Schema information common to A and C and that corresponding to B may be acquired, or schema information corresponding to A and that common to B and C may also be acquired. The CPU 100 acquires different schema information depending on a combination of designated portions. Also, a combination of designated portions that minimizes the number of pieces of schema information to be acquired can be employed to acquire pieces of schema information extracted for the combination.

In step S207, the CPU 100 outputs a schema image contained in the schema information acquired in step S206 by embedding or adding it in the document read in step S201.

After that, the user can write a diagnostic imaging finding in the schema image output in the document, creating a schema.

In the first embodiment, the image processing apparatus 1 is dedicatedly used to diagnose a human body. However, the image processing apparatus 1 is also usable to objects other than a human body. For example, the image processing apparatus 1 is applicable to create a schema based on an image for recording of the diagnostic result of an animal.

In the first embodiment, a schema image need not always be recorded in a document, and can be output in a variety of forms. For example, if necessary, a schema image can be output on a paper medium, or an obtained schema image can be recorded solely on a recording medium.

The above-described arrangement can achieve the following effects. That is, the image processing apparatus 1 provides a mechanism of automatically selecting a desired schema image to be attached to a document based on a simple operation such as input of a designated portion on a captured image by a user. Unlike the conventional apparatus, the user need not find out a desired one of schema images.

Second Embodiment

The second embodiment changes the processing procedure in the first embodiment to repeat a loop of steps S203 to S206. In the first embodiment, the processes in step S204 and subsequent steps are done after the user selects all designated portions in step S203. However, the practice of the present invention is not limited to this form.

In the second embodiment, a CPU 100 executes the processes in step S204 and subsequent steps every time the user designates a target portion in step S203. Before performing the processing in step S207, the CPU 100 displays a schema image contained in schema information selected in step S206, and then returns to step S203. In this case, every time the user designates a target portion additionally or again, a schema image contained in a schema information candidate is displayed. While viewing the schema image contained in the schema information candidate, the user confirms that schema information he wants is selected, and then ends the designated portion input operation. Finally in step S207, the CPU 100 adds the schema image confirmed by the user to a document.

This arrangement can have the following effects. That is, the user checks a schema image contained in a schema information candidate selected through a designated portion input operation. This can prevent selection of schema information containing a schema image the user does not want. The user can easily acquire a desired schema image.

Third Embodiment

The third embodiment changes the processing of step S607 shown in FIG. 6 which is a detailed description of the processing of step S206 in the processing procedure of the first embodiment. In the first embodiment, a schema information candidate with the highest level of detail is selected from a plurality of schema information candidates in step S607. However, the practice of the present invention is not limited to this form.

For example, a CPU 100 rearranges pieces of schema information acquired in step S602 or S603 based on an attribute (e.g., level of detail) contained in them. The CPU 100 presents, to the user, a list of schema images contained in the rearranged pieces of schema information by displaying the list on a monitor 104. The user selects a desired one of the displayed schema images, and instructs the CPU 100 on it with a mouse 105 or keyboard 106. In this case, the user may be allowed to select one or a plurality of schema images from the list. In response to the instruction from the user, the CPU 100 selects and acquires, as a selected schema image, schema information containing the schema image selected by the user, and outputs it in step S207 (selection output unit).

The foregoing arrangement can implement the following effect. That is, the user can composite a desired schema image in a document by only designating one or a plurality of schema images from a schema image candidate list presented by an image processing apparatus 1 in accordance with an input designated portion.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-246591 filed Sep. 25, 2008 which is hereby incorporated by reference herein in its entirety.

What is claimed is:

1. An image processing apparatus comprising:
a holding unit which holds a plurality of sets each including part information representing a human body part and a schema image serving as a schematic view of the human body part;
a unit which acquires a single image representing a body of a patient;
an acquisition unit which, when a user designates plural points having different positional coordinates on the single image, automatically acquires, from said holding unit, a schema image which is included in the set including part information common to the plural points designated on the single image by the user; and
a unit which displays the schema image acquired by said acquisition unit,
wherein said holding unit holds information in which information indicating a human body part is associated with one or more coordinates on a reference image, and
said acquisition unit acquires, when the user designates the plural points on the single image, using the information held in the holding unit, information indicating a human body part being associated with coordinates on the reference image being identical to the designated points on the single image, and acquires a schema image of the human body part indicated by the acquired information.

2. The apparatus according to claim 1, further comprising:
a unit which acquires a document; and
an output unit which records, on the acquired document, the schema image acquired by said acquisition unit, and outputs the document.

3. The apparatus according to claim 1, further comprising a unit which displays the single image.

4. The apparatus according to claim 1, further comprising a unit which detects and acquires a disorder portion from the single image,
wherein at least one of the designated points on the single image is on the acquired disorder portion.

5. The apparatus according to claim 1, wherein said acquisition unit acquires schema images included in the sets each of which includes part information globally representing a part corresponding to the plurality of designated points on the single image or part information locally representing the part corresponding to the plurality of designated points on the image.

6. An image processing method of an image processing apparatus that holds a plurality of sets each including part information representing a human body part and a schema image serving as a schematic view of the human body part, comprising the steps of:
acquiring a single captured image representing a body of a patient;
acquiring hierarchical structure information containing part information globally representing a part corresponding to a designated portion on the single captured image and part information locally representing the part corresponding to the designated portion;
when a user designates plural points having different positional coordinates on the single image, automatically acquiring from the apparatus, a schema image which is included in the set including the part information common to the plural points designated on the single image by the user; and
outputting the schema image acquired in said step of acquiring the schema image,
wherein information is held in which information indicating a human body part is associated with one or more coordinates on a reference image, and
when the user designates the plural points on the single image, using the held information, information is acquired indicating a human body part being associated with coordinates on the reference image being identical to the designated points on the single image, and a schema image is acquired of the human body part indicated by the acquired information.

7. A non-transitory computer-readable storage medium storing a computer program for causing a computer to function as:

a holding unit which holds a plurality of sets each including part information representing a human body part and a schema image serving as a schematic view of the human body part;

a unit which acquires an image representing an interior portion of a body of a patient;

an acquisition unit which, when a user designates plural points having different positional coordinates on the image, automatically acquires, from said holding unit, a schema image which is included in the set including part information common to the plural points designated on the image by the user; and a unit which displays the schema image acquired by said acquisition unit, wherein said holding unit holds information in which information indicating a human body part is associated with one or more coordinates on a reference image, and said acquisition unit acquires, when the user designates the plural points on the image, using the information held in the holding unit, information indicating a human body part being associated with coordinates on the reference image being identical to the designated points on the image, and acquires a schema image of the human body part indicated by the acquired information.

8. The apparatus according to claim 1, wherein said holding unit holds plural schema images in association with hierarchical structure information containing part information locally representing the human body part, and said acquisition unit acquires a schema image corresponding to a human body part common to part information included in hierarchical structure information corresponding to the designated points.

9. The apparatus according to claim 8, further comprising a display control unit which displays on a display unit a schema image corresponding to a human body part common to part information included in hierarchical structure information corresponding to the designated points.

10. The apparatus according to claim 1, wherein said acquisition unit acquires, when said acquisition unit cannot acquire the schema image which is included in the set including part information common to the plural points designated on the single image by the user, a schema image which is included in the set including part information for each of the plural points designated on the single image by the user.

11. The apparatus according to claim 1, wherein said acquisition unit acquires, when said acquisition unit acquires plural schema images each of which is included in the set including part information common to the plural points designated on the single image by the user, the schema image which is included in the set which includes part information representing a most local part.

* * * * *